(12) United States Patent
Stevens et al.

(10) Patent No.: US 11,515,038 B2
(45) Date of Patent: Nov. 29, 2022

(54) GENERATING AND EVALUATING DYNAMIC PLANS UTILIZING KNOWLEDGE GRAPHS

(71) Applicant: International Business Machines Corporation, Armonk, NY (US)

(72) Inventors: Richard J. Stevens, Monkton, VT (US); Fernando Jose Suarez Saiz, Armonk, NY (US)

(73) Assignee: International Business Machines Corporation, Armonk, NY (US)

( * ) Notice: Subject to any disclaimer, the term of this patent is extended or adjusted under 35 U.S.C. 154(b) by 1027 days.

(21) Appl. No.: 16/212,683

(22) Filed: Dec. 7, 2018

(65) Prior Publication Data

US 2020/0185098 A1 Jun. 11, 2020

(51) Int. Cl.
| | |
|---|---|
| G16H 50/20 | (2018.01) |
| G16H 20/00 | (2018.01) |
| G16H 40/20 | (2018.01) |
| G16H 10/60 | (2018.01) |
| G06N 5/02 | (2006.01) |

(52) U.S. Cl.
CPC ............ G16H 50/20 (2018.01); G06N 5/022 (2013.01); G16H 10/60 (2018.01); G16H 20/00 (2018.01); G16H 40/20 (2018.01)

(58) Field of Classification Search
CPC ........ G16H 50/20; G16H 10/60; G16H 20/00; G16H 40/20; G16H 70/20; G16H 70/60; G06N 5/022; G06N 5/04
See application file for complete search history.

(56) References Cited

U.S. PATENT DOCUMENTS

| | | | | |
|---|---|---|---|---|
| 7,260,480 B1 * | 8/2007 | Brown | ................... | G16H 70/60 |
| | | | | 703/11 |
| 8,566,121 B2 | 10/2013 | Ramasubramanian et al. | | |
| 10,614,919 B1 * | 4/2020 | Yedwab | ................. | G16H 10/60 |
| 11,302,449 B2 * | 4/2022 | Farha | .................... | G16H 70/20 |
| 2012/0129139 A1 * | 5/2012 | Partovi | .................. | G16H 40/67 |
| | | | | 434/262 |
| 2013/0185119 A1 | 7/2013 | Palao et al. | | |

(Continued)

FOREIGN PATENT DOCUMENTS

| | | | | |
|---|---|---|---|---|
| CN | 103997516 A | | 8/2014 | |
| WO | WO-2015009682 A1 * | | 1/2015 | ............. G06N 5/022 |

*Primary Examiner* — Ryan W Sherwin
(74) *Attorney, Agent, or Firm* — Patterson + Sheridan, LLP

(57) ABSTRACT

Techniques for evaluating dynamically modified plans are provided. A selection of a treatment plan template is received, where the treatment plan template specifies a plurality of treatment stages, where each treatment stage defines a plurality of treatment options. A plurality of modifications to the treatment plan template is generated. It is determined, for each respective modification of the plurality of modifications, whether the respective modification is permissible, based on one or more predefined institutional criteria. Upon determining that a first modification of the plurality of modifications is permissible, a first treatment plan is generated based on the first modification to the treatment plan template. Further, a first predicted efficacy measure is generated for the first treatment plan based on analyzing a knowledge graph. Finally, the first treatment plan is provided, along with at least an indication of the first predicted efficacy measure.

20 Claims, 12 Drawing Sheets

(56) References Cited

U.S. PATENT DOCUMENTS

| | | | |
|---|---|---|---|
| 2018/0089385 A1* | 3/2018 | Gupta | G16H 50/20 |
| 2018/0102190 A1 | 4/2018 | Hogue et al. | |
| 2018/0137249 A1 | 5/2018 | Eggebraaten et al. | |
| 2018/0240552 A1* | 8/2018 | Tuyl | G16H 50/20 |
| 2019/0189287 A1* | 6/2019 | Livesay | G16H 50/70 |

* cited by examiner

GENERATING AND EVALUATING DYNAMIC PLANS UTILIZING KNOWLEDGE GRAPHS

BACKGROUND

The present disclosure relates to knowledge graphs, and more specifically, to generating and scoring potential therapies based on evaluating knowledge graphs and real world evidence.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

Additionally, when patients are to be treated, healthcare providers rely on defined treatments or therapies, and cannot identify new or modified therapies that may be better than existing accepted approaches. With current advancements in medical treatments, alternative, new, or better treatments are becoming available frequently. However, given the rapid pace and complexity of the published literature, it is impossible for healthcare providers to identify and evaluate these potential therapies. Thus, patient outcomes are often worse than they could be, because the accepted set of treatment plans cannot consider or include potential new treatment options without significant time and expense.

SUMMARY

According to one embodiment of the present disclosure, a method is provided. The method includes receiving a selection of a treatment plan template, wherein the treatment plan template specifies a plurality of treatment stages, wherein each treatment stage defines a plurality of treatment options, and generating a plurality of modifications to the treatment plan template. The method further includes determining, for each respective modification of the plurality of modifications, whether the respective modification is permissible, based on one or more predefined institutional criteria. Upon determining that a first modification of the plurality of modifications is permissible, the method includes generating a first treatment plan based on the first modification to the treatment plan template. Additionally, the method includes generating a first predicted efficacy measure for the first treatment plan by operation of one or more processors, based on analyzing a knowledge graph. Finally, the method includes providing the first treatment plan, along with at least an indication of the first predicted efficacy measure.

According to a second embodiment of the present disclosure, a computer-readable storage medium is provided. The computer-readable storage medium has computer-readable program code embodied therewith, the computer-readable program code executable by one or more computer processors to perform an operation. The operation includes receiving a selection of a treatment plan template, wherein the treatment plan template specifies a plurality of treatment stages, wherein each treatment stage defines a plurality of treatment options, and generating a plurality of modifications to the treatment plan template. The operation further includes determining, for each respective modification of the plurality of modifications, whether the respective modification is permissible, based on one or more predefined institutional criteria. Upon determining that a first modification of the plurality of modifications is permissible, the operation includes generating a first treatment plan based on the first modification to the treatment plan template. Additionally, the operation includes generating a first predicted efficacy measure for the first treatment plan based on analyzing a knowledge graph. Finally, the operation includes providing the first treatment plan, along with at least an indication of the first predicted efficacy measure.

According to a third embodiment of the present disclosure, a system is provided. The system includes one or more computer processors and a memory containing a program which when executed by the one or more computer processors performs an operation. The operation includes receiving a selection of a treatment plan template, wherein the treatment plan template specifies a plurality of treatment stages, wherein each treatment stage defines a plurality of treatment options, and generating a plurality of modifications to the treatment plan template. The operation further includes determining, for each respective modification of the plurality of modifications, whether the respective modification is permissible, based on one or more predefined institutional criteria. Upon determining that a first modification of the plurality of modifications is permissible, the operation includes generating a first treatment plan based on the first modification to the treatment plan template. Additionally, the operation includes generating a first predicted efficacy measure for the first treatment plan based on analyzing a knowledge graph. Finally, the operation includes providing the first treatment plan, along with at least an indication of the first predicted efficacy measure.

DETAILED DESCRIPTION

Figure 1:
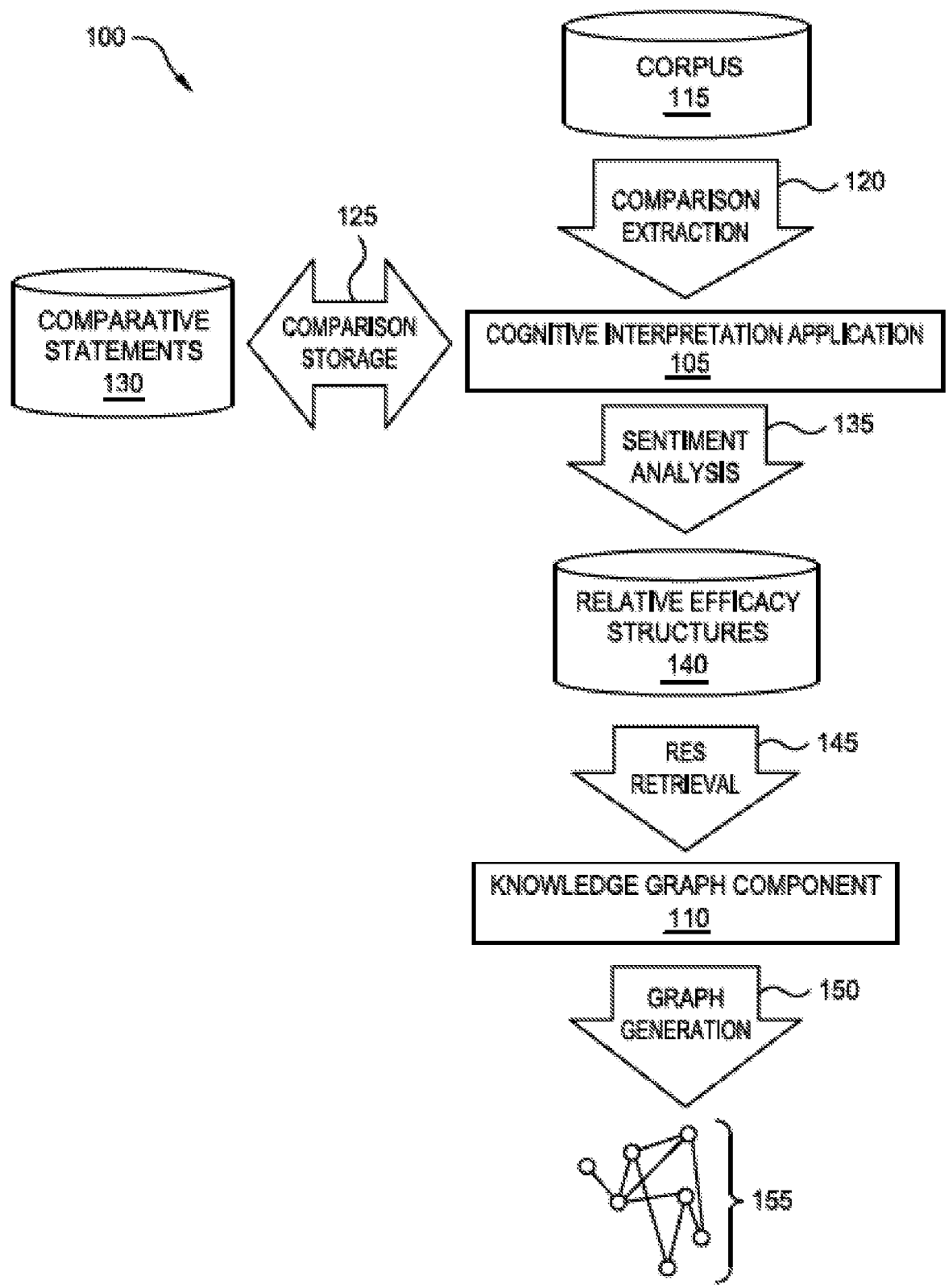
FIG. 1 illustrates a workflow for cognitively determining the relative efficacy of therapies, according to one embodiment disclosed herein.

In embodiments of the present disclosure, potential treatment plans are identified and evaluated for patients based on information contained in a knowledge graph, and based on real world evidence (RWE). In an embodiment, a set of treatment plan templates are used to plan out a treatment or therapy regimen for patients. In one embodiment, each disorder or malady is associated with a set of accepted plan templates, which healthcare providers can select from. In some embodiments, each treatment plan template includes a series of treatment stages (which may overlap, or may be arranged sequentially, with any amount of time between stages), where each stage includes one or more specific options. For example, a template for treating a particular type of cancer may specify a first stage corresponding to an initial radiation treatment, followed by a second stage for chemotherapy, and a third stage for an additional drug therapy. In an embodiment, each of these stages can include specific or particular options (e.g., a particular type or configuration for the radiation, chemotherapy, and medications). In embodiments, healthcare providers can select a template, as well as select the individual options at each stage of treatment.

In existing systems, healthcare providers are limited to the defined plan templates, which can cause superior treatments or therapies to be ignored. In embodiments of the present disclosure, treatment plan templates are modified based on a variety of criteria, and a set of new treatment plans are generated based on the modified templates. Further, in some embodiments, healthcare providers can manually specify new treatment plans or template modifications. In an embodiment, each new treatment plan is then evaluated based on published clinical study results (e.g., contained in a knowledge graph) and/or RWE (e.g., extracted from electronic medical records, or EMRs). In this way, potential new treatments can be identified and scored, which can improve patient outcomes.

Based on these potential new therapies, the healthcare provider can make more informed decisions about up-to-date therapies and comparisons based on a knowledge graph and RWE that takes into account new literature and records as they are produced. In some embodiments of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 150. In some embodiments, a Knowledge Graph 150 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement(s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130. In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud). As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store, and performs Graph Generation 150 to generate a Knowledge Graph 155. In an embodiment, each node in the Knowledge Graph 150 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

Although not depicted in the illustrated embodiment, in some embodiments, the Cognitive Interpretation Application 105 also identifies statements relating to the efficacy or outcomes of a therapy, even in the absence of a comparison between therapies. In such an embodiment, the Cognitive Interpretation Application 105 can also perform Sentiment Analysis 135 on the non-comparative statements to determine whether the therapy is being referred to in a positive, neutral, or negative manner. In some embodiments, the Cognitive Interpretation Application 105 also determines the efficacy and/or outcomes of the therapy, if available in the Corpus 115. For example, in such an embodiment, the Cognitive Interpretation Application 105 can determine what percentages of patients benefitted (with respect to each potential outcome), the magnitude of the benefits, and the like. In an embodiment, the Knowledge Graph Component 110 then incorporates these non-comparative statements into the Knowledge Graph 155 (e.g., by adding or refining a node corresponding to the therapy being discussed).

Figure 2:
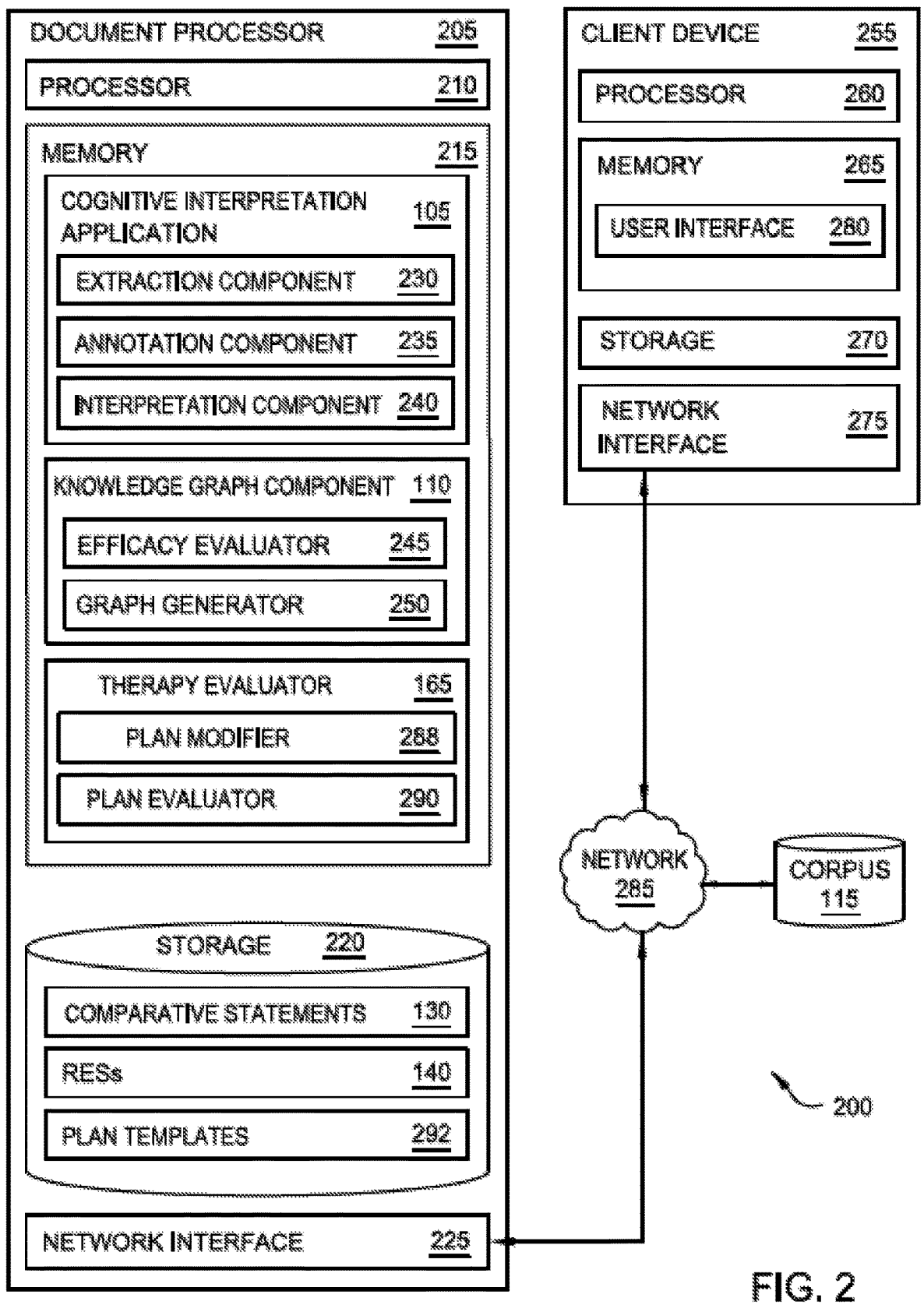
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115. Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130, RESs 140, and Plan Templates 292. In some embodiments, as discussed above, the Comparative Statements 130, RESs 140, and/or Plan Templates 292 may be stored in one or more remote storage locations, such as in the cloud. Further, in some embodiments, the Storage 220 includes non-comparative statements as well. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

In an embodiment, the Plan Templates 292 are used to design treatment paths for patients. In one embodiment, each Plan Template 292 specifies a set of stages of treatment, and each stage includes a set of specific options for treatment. In some embodiments, the Plan Templates 292 are defined by SMEs, such as standards-setting entities. In an embodiment, a Plan Template 292 is used to design a treatment plan by selecting a designated option for each of the stages. In some embodiments, the Plan Templates 292 includes stages, but one or more stages may not include specific options. For example, a stage may indicate that chemotherapy should be used, but leave the particulars up to the treating physician. In embodiments, these treatment plans are evaluated in order to determine whether they are acceptable or efficacious for treating individual patients, as discussed in more detail below.

In the illustrated embodiment, the Memory 215 of the Document Processor 205 includes a Cognitive Interpretation Application 105, a Knowledge Graph Component 110, and a Therapy Evaluator 165. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs. As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

In the illustrated embodiment, the Therapy Evaluator 165 includes a Plan Modifier 288 and a Plan Evaluator 290. Although depicted as discrete components for illustration, in embodiments, the operations and functionality of the Plan Modifier 288 and Plan Evaluator 290 can be combined or divided across any number of components. Further, although depicted as software components residing in Memory 215, in embodiments, the operations and functionality of the Plan Modifier 288 and Plan Evaluator 290 can be implemented using hardware, software, or a combination of hardware and software.

In an embodiment, the Therapy Evaluator 165 analyzes the knowledge graph to modify Plan Templates 292, generate treatment plans based on the modified templates, and evaluate or score the generated plans. In the illustrated embodiment, the Plan Modifier 288 receives a selection of a Plan Template 292. In some embodiments, the Plan Modifier 288 receives information relating to one or more patients, and identifies Plan Templates 292 that may be relevant (e.g., based on attributes of the patient, and/or the disorder to be treated). In one embodiment, the Plan Modifier 288 receives an indication of a particular patient or patient profile, and determines a corresponding cohort for the patient (e.g., based on attributes of the patient found in the patient profile, electronic medical records (EMRs), or specified by the healthcare provider or patient).

Once one or more Plan Templates 292 are identified or received, in one embodiment, the Plan Modifier 288 generates one or more modifications for each Plan Template 292, as discussed below in more detail. In one embodiment, the modifications can include adding additional stages, removing one or more stages, adding additional options to one of the stages, and the like. In some embodiments, the healthcare provider can also specify or manually generate modifications or new treatment plans, which can be evaluated and scored against existing treatment plans in order to determine their potential efficacy, as discussed below in more detail.

In one embodiment, once this set of treatment plans is generated, the Plan Evaluator 290 parses the knowledge graph and/or RWE to score and rank the set of plans based on a variety of factors. For example, in one embodiment, the Scoring Component 292 scores therapies based on how effective they are expected to be, and their relative efficacy as compared to each other. In one embodiment, analyzing the knowledge graph to generate a score for a treatment plan includes searching the graph for evidence to support (or discourage) all or a portion of the treatment plan. In some embodiments, the Plan Evaluator 290 also considers RWE when evaluating the treatment plans. In an embodiment, to analyze RWE, the Plan Evaluator 290 identifies patients that are (or were) similarly situated to the index patient (e.g., patients in the same cohort with the same disorder), and evaluates the treatment plan(s) followed by each of those patients, as well as the eventual outcomes of those patients.

In some embodiments, the Plan Evaluator 290 evaluates plans generated based on modified treatment plan templates. In some embodiments, the Plan Evaluator 290 similarly evaluates plans that are generated based on unmodified treatment plan templates, in order to determine whether each of the new treatment plans is likely to be superior, may be a useful alternative that is equally effective, or is likely inferior. In this way, patient outcomes can be improved, because healthcare providers are not limited to the bounded set of accepted therapies, and can understand and review the evidence supporting or discouraging particular combinations and selections of treatment options, at various stages of treatment.

In the illustrated embodiment, the Client Device 255 includes a Processor 260, a Memory 265, and Storage 270. In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105, Knowledge Graph Component 110, and Therapy Suggestion Application 165 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs. Additionally, in an embodiment, the APIs associated with the Therapy Evaluator 165 allow the user to enter and/or generate treatment plans, and to receive evaluations for each plan.

Figure 3A:
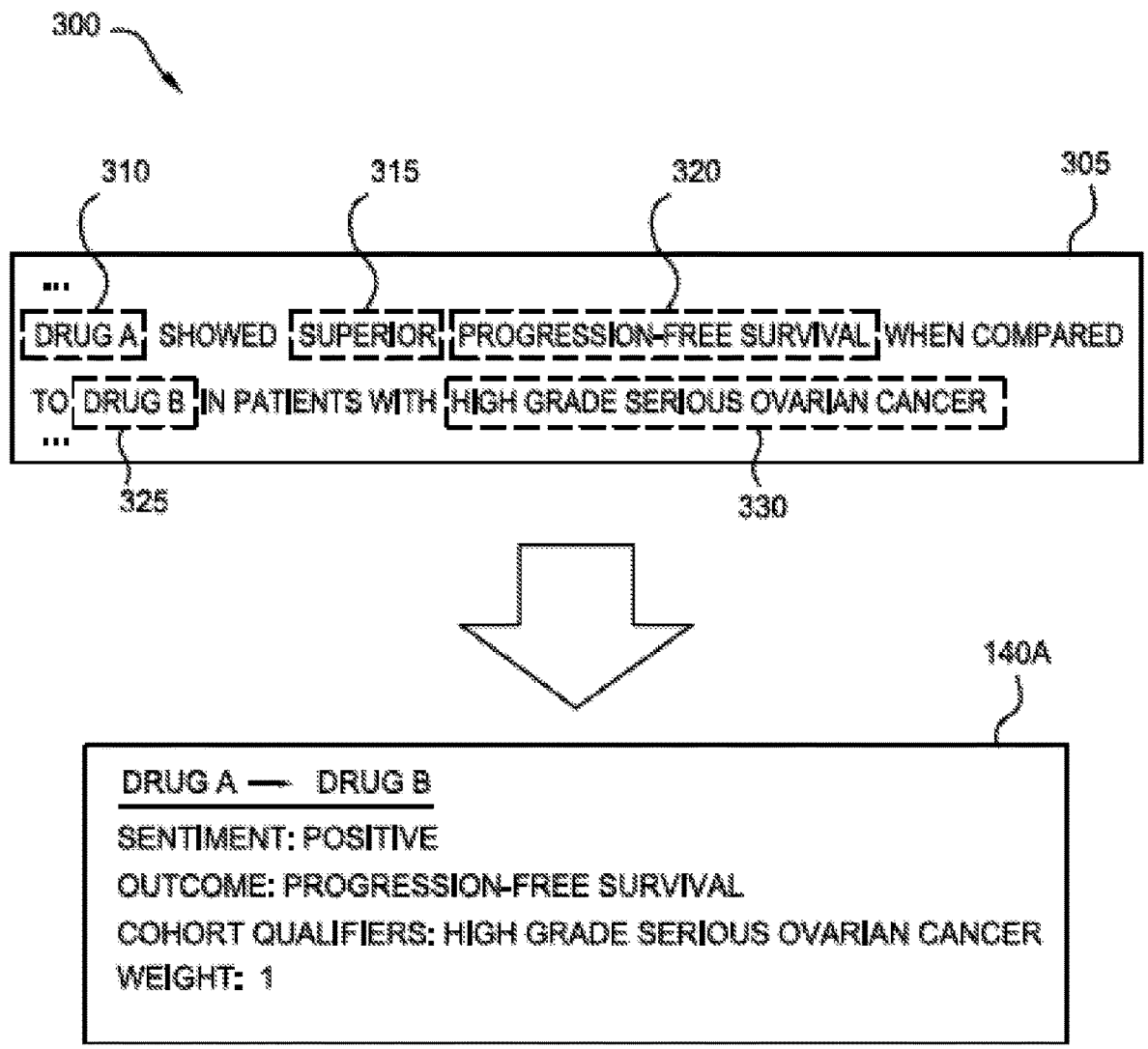
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
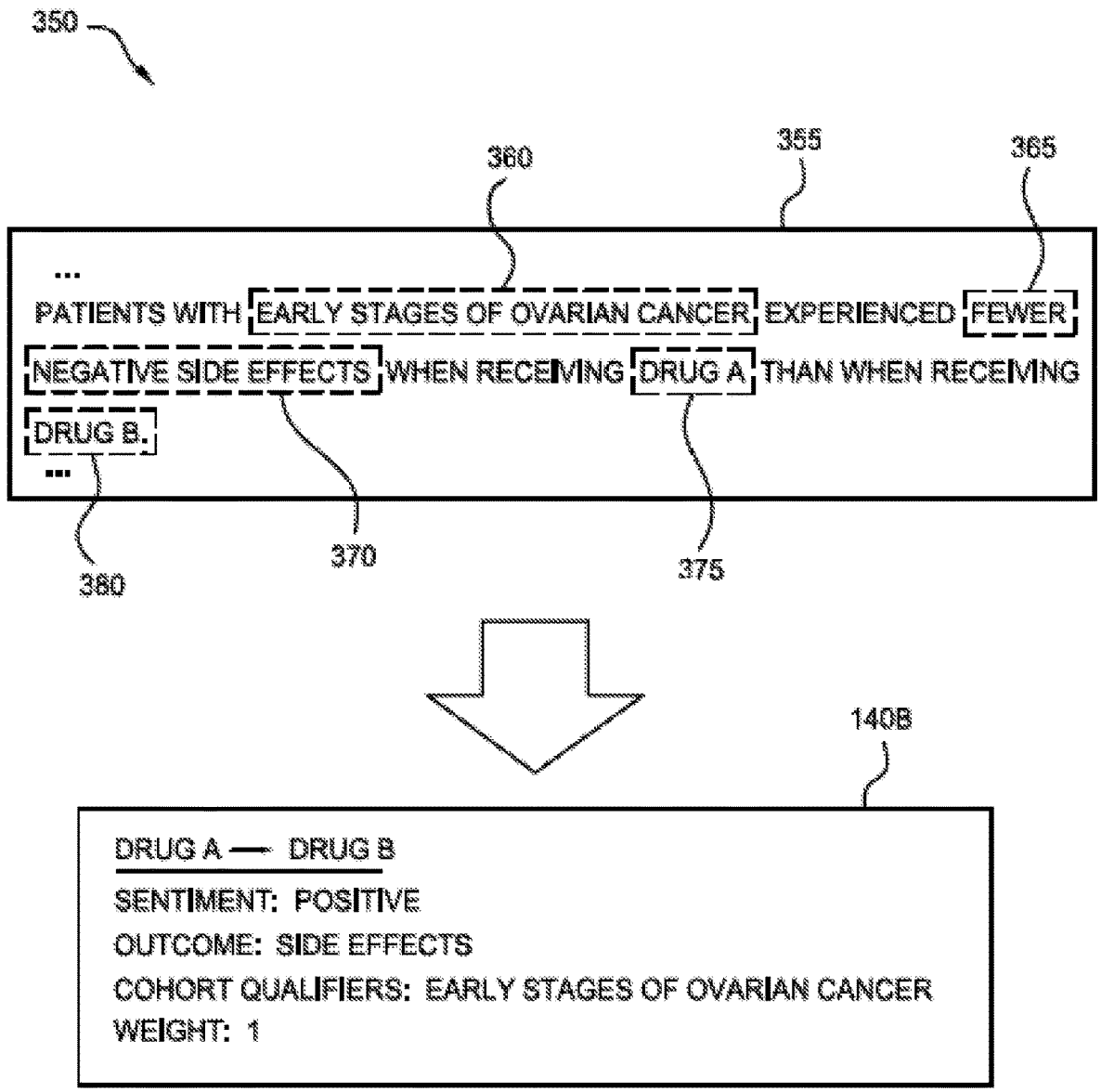
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
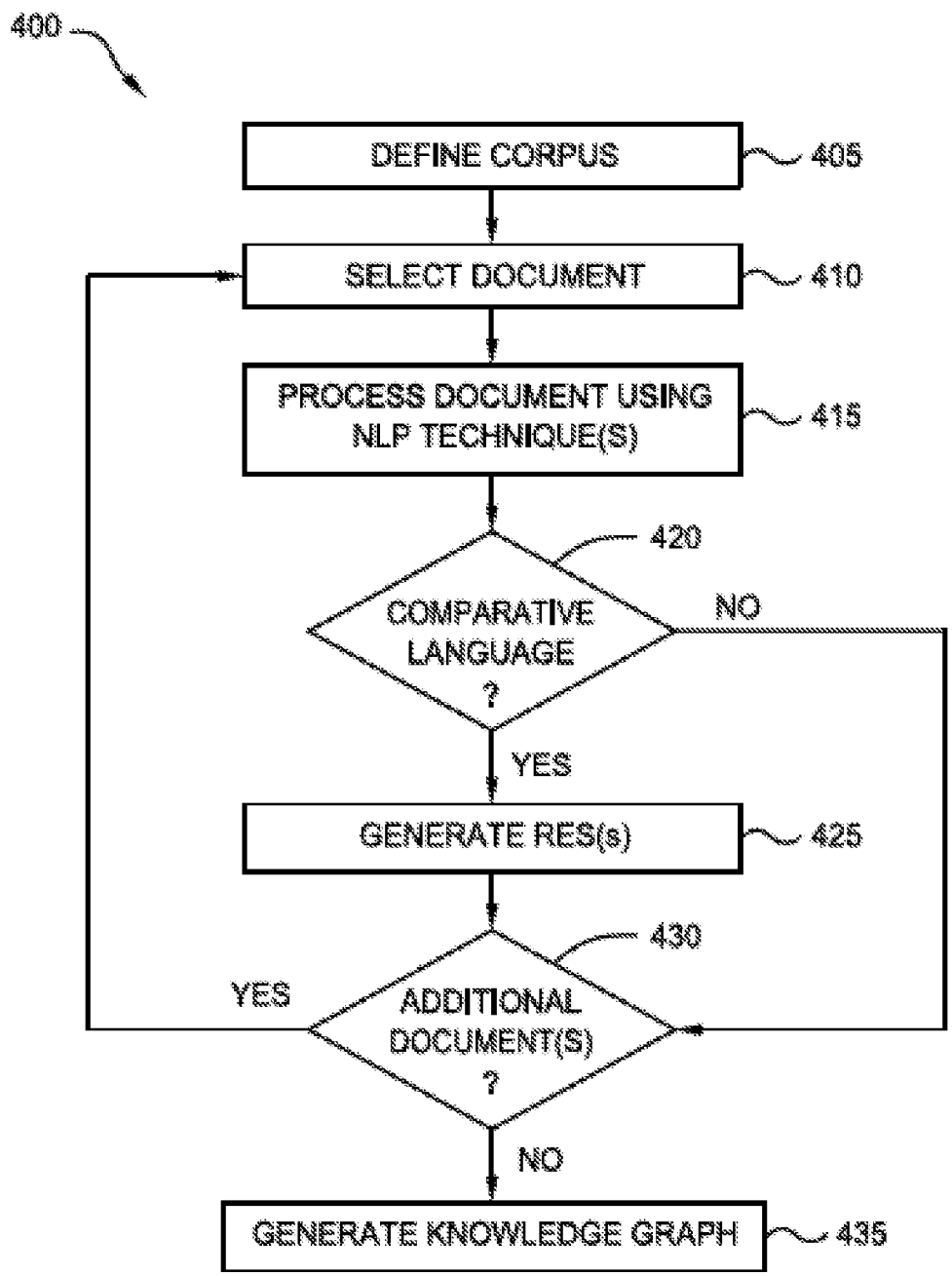
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or sub-corpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
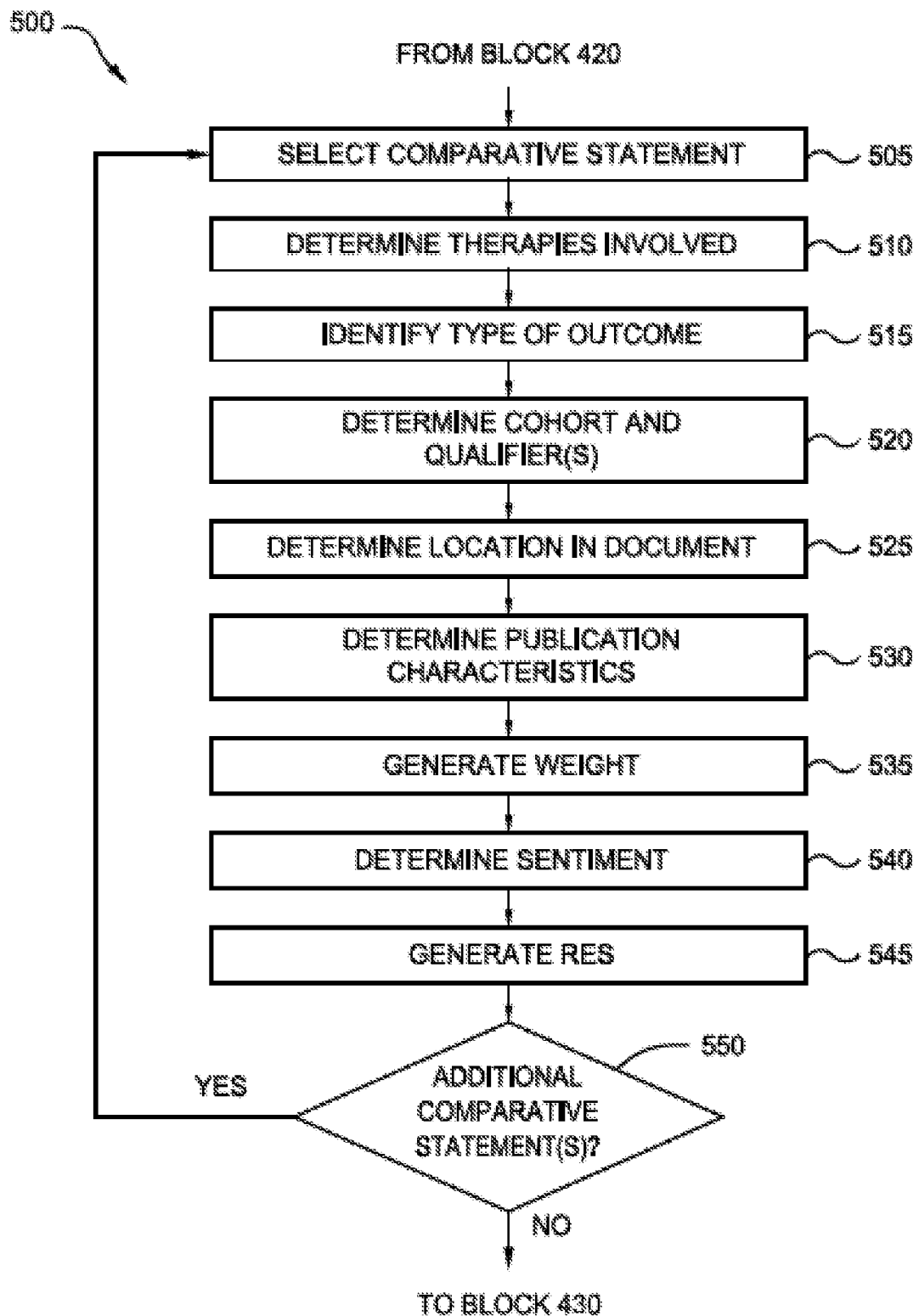
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
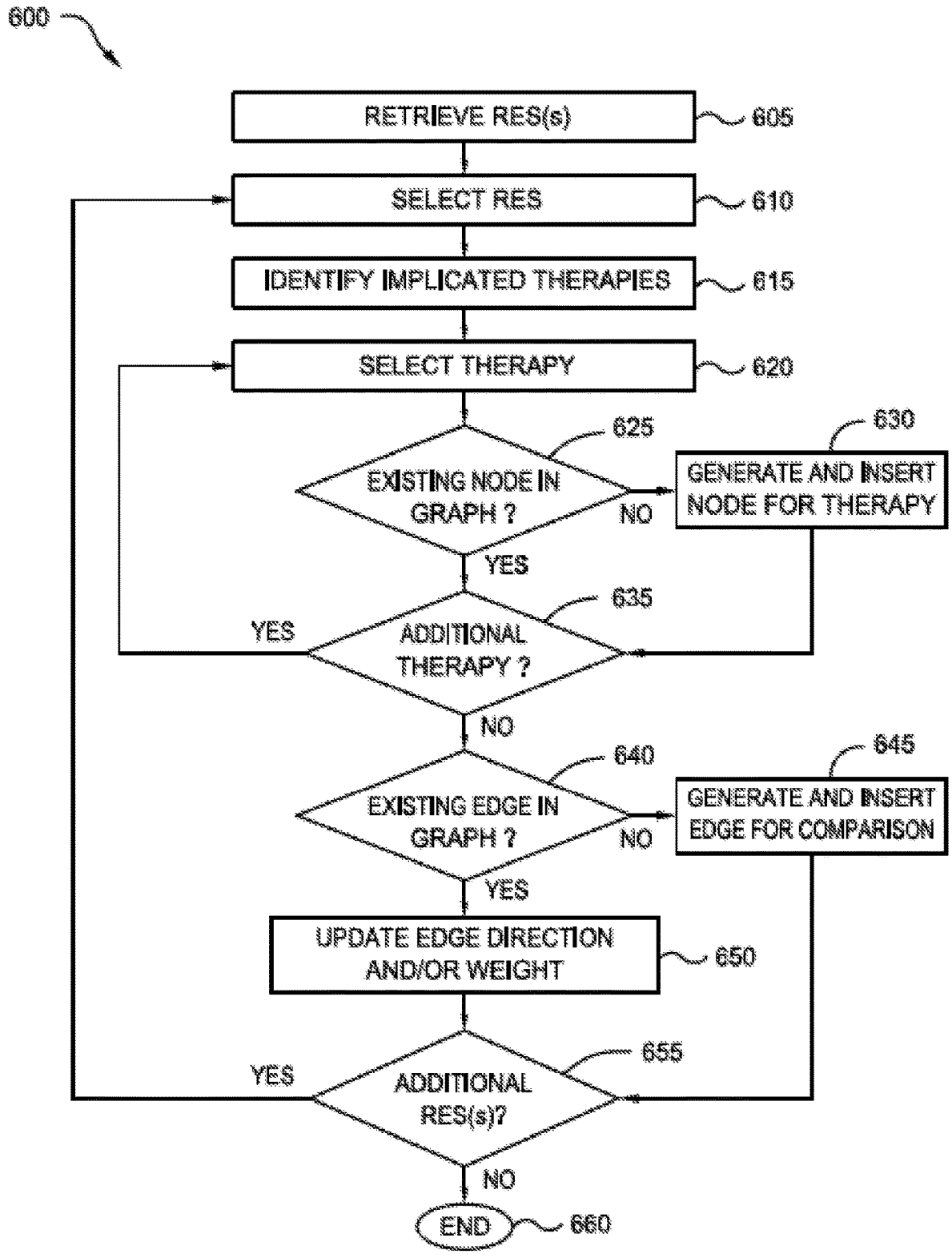
FIG. 6 is a flow diagram illustrating a method for generating a knowledge graph based on generated relative efficacy structures, according to one embodiment disclosed herein.

FIG. 6 is a flow diagram illustrating a method 600 for generating a knowledge graph based on generated relative efficacy structures, according to one embodiment disclosed herein. The method 600 begins at block 605, where the Knowledge Graph Component 110 retrieves one or more RES(s) 140 that were generated by the Cognitive Interpretation Application 105. At block 610, the Knowledge Graph Component 110 selects one of the RESs 140. The method 600 then proceeds to block 615, where the Knowledge Graph Component 110 identifies the therapies that are indicated by the selected RES 140. That is, the Knowledge Graph Component 110 determines which therapies are compared in the RES 140. At block 620, the Knowledge Graph Component 110 selects one of these identified therapies.

The method 600 continues to block 625, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 600 continues to block 635. If the selected therapy is not yet in the knowledge graph, the method 600 proceeds to block 630, where the Knowledge Graph Component 110 generates and inserts a new node into the graph to represent the selected therapy. The method 600 then continues to block 635.

At block 635, the Knowledge Graph Component 110 determines whether there are additional therapies in the selected RES 140. If so, the method 600 returns to block 620. Otherwise, the method 600 continues to block 640. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 640, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 640, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 640, 645, and 650) is repeated for each.

If the Knowledge Graph Component 110 determines, at block 640, that there is no edge in the graph representing the comparison, with respect to the identified cohort and outcome, the method 600 continues to block 645, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 640, that an edge already exists for the indicated comparison, with respect to the specified cohort and outcome, the method 600 continues to block 650, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 600 then proceeds to block 655, where the Knowledge Graph Component 110 determines whether there is at least one additional RES 140 that has not been analyzed and ingested into the knowledge graph. If so, the method 600 returns to block 610 to select a next RES 140. Otherwise, the method 600 terminates at block 660. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Although not illustrated, in some embodiments, the Knowledge Graph Component 110 can further generate nodes for which there are no existing comparisons. For example, if a paper or article includes a study of a particular therapy, but does not include any comparison to other therapies, the Knowledge Graph Component 110 can generate a node for the therapy, without necessarily connecting the node to any other therapies. Further, in some embodiments, the Knowledge Graph Component 110 includes an indication as to the efficacy of each therapy. For example, in such an embodiment, the Cognitive Interpretation Application 105 can determine the overall efficacy for each particular therapy, in addition to determining the relative efficacies of therapies, as compared to each other. This information can then be included in the corresponding node in the knowledge graph. In embodiments, the efficacy can include a percentage of patients who the therapy helped, and/or an amount that the therapy helped.

Figure 7:
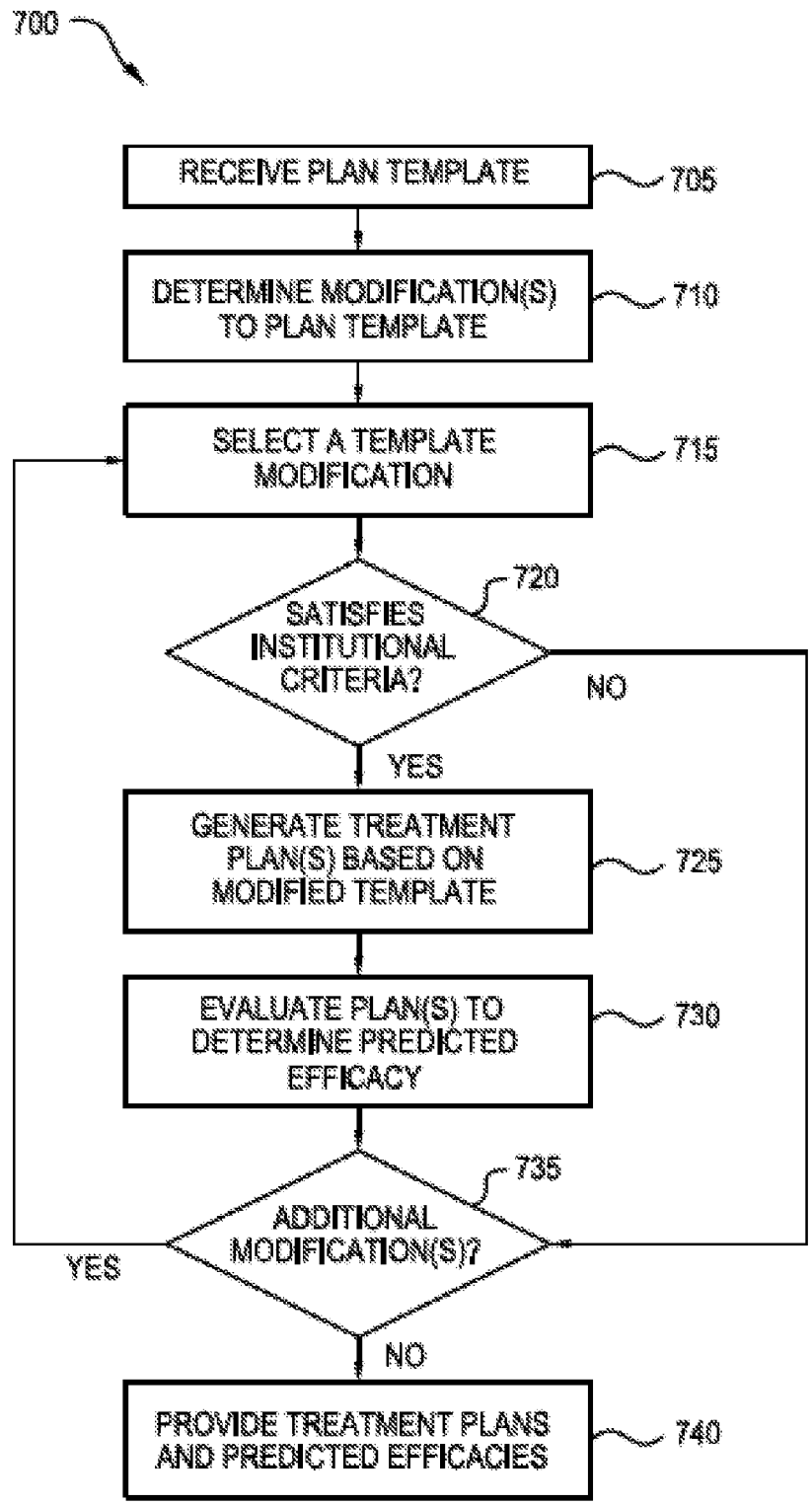
FIG. 7 is a flow diagram illustrating a method for generating and evaluating treatment plans, according to one embodiment disclosed herein.

FIG. 7 is a flow diagram illustrating a method 700 for generating and evaluating treatment plans, according to one embodiment disclosed herein. The method 700 begins at block 705, where the Therapy Evaluator 165 receives a treatment plan template. In one embodiment, this template is selected by a healthcare provider, based on a particular patient to be treated (referred to herein as the index patient). In some embodiments, the Therapy Evaluator 165 receives an indication of the patient (e.g., a patient profile, a set of attributes, and the like), and selects one or more templates based on these attributes (e.g., based on the disorder to be treated, and/or one or more other attributes of the patient). The method 700 then proceeds to block 710, where the Therapy Evaluator 165 determines one or more modifications to the plan template. In one embodiment, this includes generating, by the Therapy Evaluator 165, a set of potential modifications, as discussed in more detail below with reference to FIG. 8. In some embodiments, this also includes receiving one or more modifications from the user. The Therapy Evaluator 165 then selects one of the identified or generated template modifications at block 715.

The method 700 then proceeds to block 720, where the Therapy Evaluator 165 determines whether the modification complies with predefined criteria. In some embodiments, these criteria are specified by standards-setting bodies. In one embodiment, the institutional criteria are associated with the entity that the healthcare provider works for. For example, in an embodiment, a particular clinic or hospital may specify that certain templates may not be modified, or that particular stages in one or more templates are not modifiable. Similarly, the criteria may include an indication that a particular template can be modified, but it must always include a particular stage (e.g., that one or more stages are not removable and must be present). In one embodiment, the criteria include availability of particular treatment options in a current practice setting or geographical region. For example, in some embodiments, a particular medication may be unavailable in certain countries. If the selected modification does not comply with the predefined criteria, the Therapy Evaluator 165 discards the modification, and the method 700 proceeds to block 735.

If, at block 720, the Therapy Evaluator 165 determines that the modification complies with the institutional criteria, the method 700 continues to block 725, where the Therapy Evaluator 165 generates one or more treatment plans based on the selected modified template. For example, in an embodiment, the modified template can include any number of stages of treatment, each with any number of treatment options. In an embodiment, the Therapy Evaluator 165 is configured to evaluate the efficacy of multiple potential plans based on the template (e.g., multiple combinations of options), and generates a set of treatment plans to reflect these combinations. In some embodiments, the Therapy Evaluator 165 generates a set of plans that cover all possible combinations of treatment options in the modified template. The method 700 then proceeds to block 730.

At block 730, the Therapy Evaluator 165 evaluates each of the generated plans in order to determine their predicted efficacy. In an embodiment, this includes analyzing a knowledge graph, as well as analyzing available RWE, as discussed in more detail below with reference to FIGS. 9 and 10, respectively. Once the plans have been evaluated and scored, the method 700 continues to block 735, where the Therapy Evaluator 165 determines whether there are additional modifications to be tested. If so, the method 700 returns to block 715. Otherwise, the method 700 proceeds to block 740. At block 740, the Therapy Evaluator 165 provides the generated treatment plans to a user, as well as an indication of the predicted efficacies. In one embodiment, the predicted efficacies are relative efficacies, indicating which treatments are predicted to be superior to others. In some embodiments, the predicted efficacy includes an overall or absolute efficacy (e.g., a prediction as to the likelihood of improvement). In one embodiment, the Therapy Evaluator 165 only provides plans above a defined threshold of efficacy or confidence. In some embodiments, the Therapy Evaluator 165 provides a predefined number of plans (e.g., the ten best). In an embodiment, the Therapy Evaluator 165 only provides plans that are expected to be superior to plans generated based on the non-modified template.

In some embodiments, prior to providing the scored and ranked treatment plans, the Therapy Evaluator 165 aggregates the generated scores with respect to the template used to generate the corresponding plan. For example, in such an embodiment, the Therapy Evaluator 165 can identify all treatment plans that were generated using a first template, and aggregate their scores. In embodiments, this aggregation can include summing, averaging, and the like. In one embodiment, the Therapy Evaluator 165 then presents a scored and ranked set of templates, such that the user can determine which modifications tend to result in superior outcomes.

Figure 8:
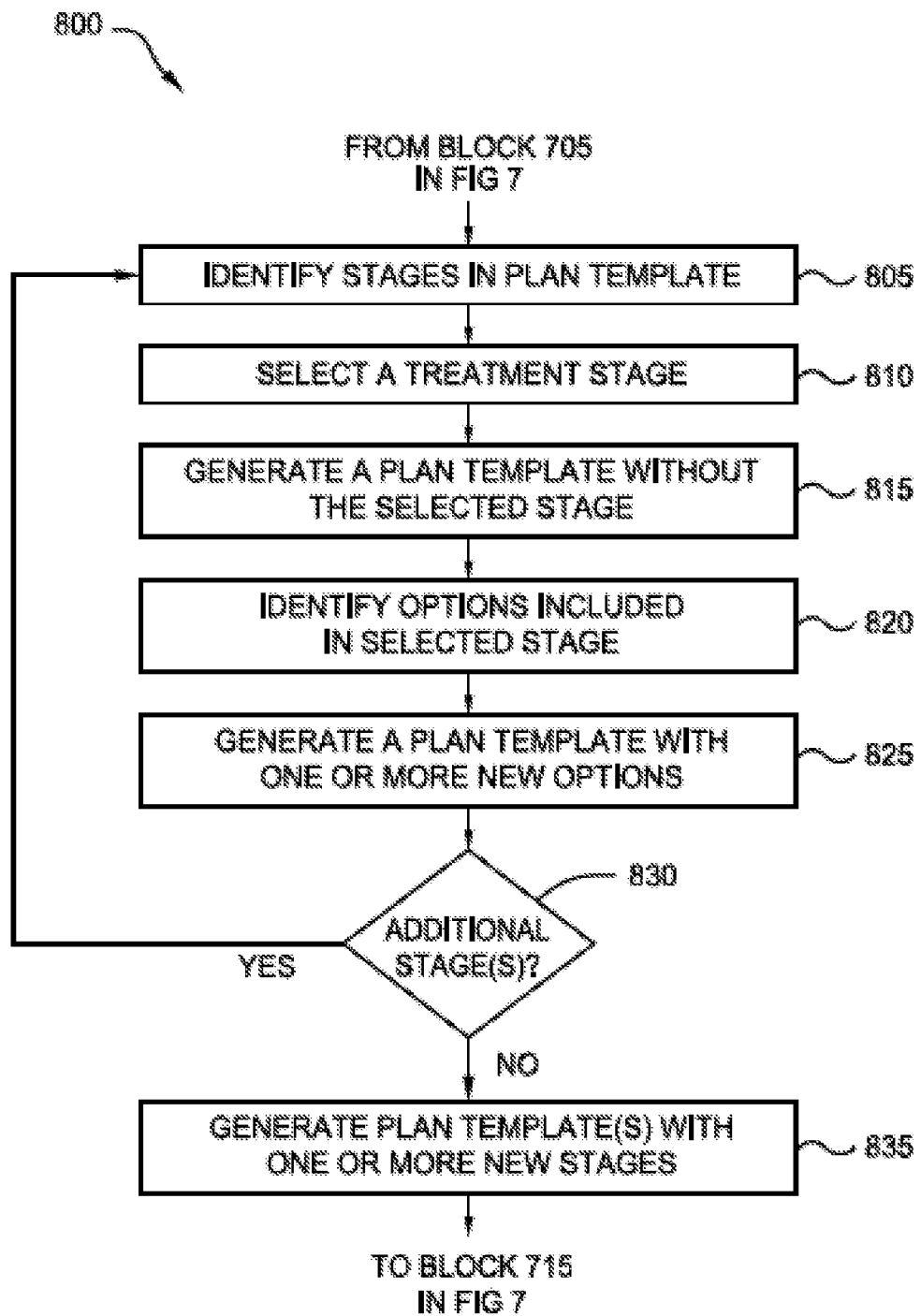
FIG. 8 is a flow diagram illustrating a method for modifying treatment plan templates, according to one embodiment disclosed herein.

FIG. 8 is a flow diagram illustrating a method 800 for modifying treatment plan templates, according to one embodiment disclosed herein. In one embodiment, the method 800 corresponds to block 710 in FIG. 7. The method 800 begins at block 805, where the Therapy Evaluator 165 identifies the stages that exist in the selected or indicated treatment plan. As discussed above, in embodiments, each treatment plan includes a set of treatment stages. These stages may overlap partially or entirely (e.g., two or more therapies or treatments provided simultaneously), or may be sequential. In some embodiments, the stages may include a defined length of time for each stage and/or between stages. In one embodiment, the transitions are defined by triggering events, as specified in the template.

The method 800 then proceeds to block 810, where the Therapy Evaluator 165 selects one of the identified stages. At block 815, the Therapy Evaluator 165 generates one or more modified plan templates that do not include the selected stage. The method 800 continues to block 820, where the Therapy Evaluator 165 identifies the treatment options specified in the selected stage. At block 825, the Therapy Evaluator 165 generates one or more modified templates that include one or more new options for the selected stage. In one embodiment, the Therapy Evaluator 165 determines these new options based in part on the existing options in the stage. In some embodiments, the Therapy Evaluator 165 identifies new options based on a title or label associated with the stage (e.g., a "chemotherapy" label). In one embodiment, the Therapy Evaluator 165 searches one or more knowledge graphs based on the existing options and/or label, in order to identify potential new treatment options. In some embodiments, this search is further constrained based on the cohort or attributes of the intended index patient.

In one embodiment, identifying new potential options includes identifying other treatments in the same class as the existing options. For example, if one option is a type of anti-inflammatory medication, the Therapy Evaluator 165 may identify other drugs that are also anti-inflammatories. The method 800 then continues to block 830, where the Therapy Evaluator 165 determines whether there are any additional stages to be considered. If so, the method 800 returns to block 810. If not, the method 800 proceeds to block 835, where the Therapy Evaluator 165 generates one or more modified plan templates that include one or more additional stages not currently included in the template. In one embodiment, the Therapy Evaluator 165 analyzes other related templates (e.g., other treatment templates that are intended to treat the same disorder) to identify potential new stages for the selected template. Further, in one embodiment, the Therapy Evaluator 165 searches one or more knowledge graphs based on the existing stages and/or template label, in order to identify new potential stages. The method 800 then terminates.

In embodiments, the Therapy Evaluator 165 can generate any combination of the above-discussed combinations. For example, in addition to generating a modified template that lacks one stage, the Therapy Evaluator 165 can generate modified templates with two or more stages removed. Similarly, the Therapy Evaluator 165 can generate a modified template with one or more new treatment options for multiple stages. Further, in an embodiment, the Therapy Evaluator 165 can generate modified templates that remove one or more stages, add one or more new options, and/or add one or more new stages. In some embodiments, the user can specify which type(s) of modification they prefer or are most interested in. This may be in the form of instructing the Therapy Evaluator 165 to only consider such modifications, or may include weighting these modifications more heavily, so that more of them are generated as compared to modifications of lesser importance.

Figure 9:
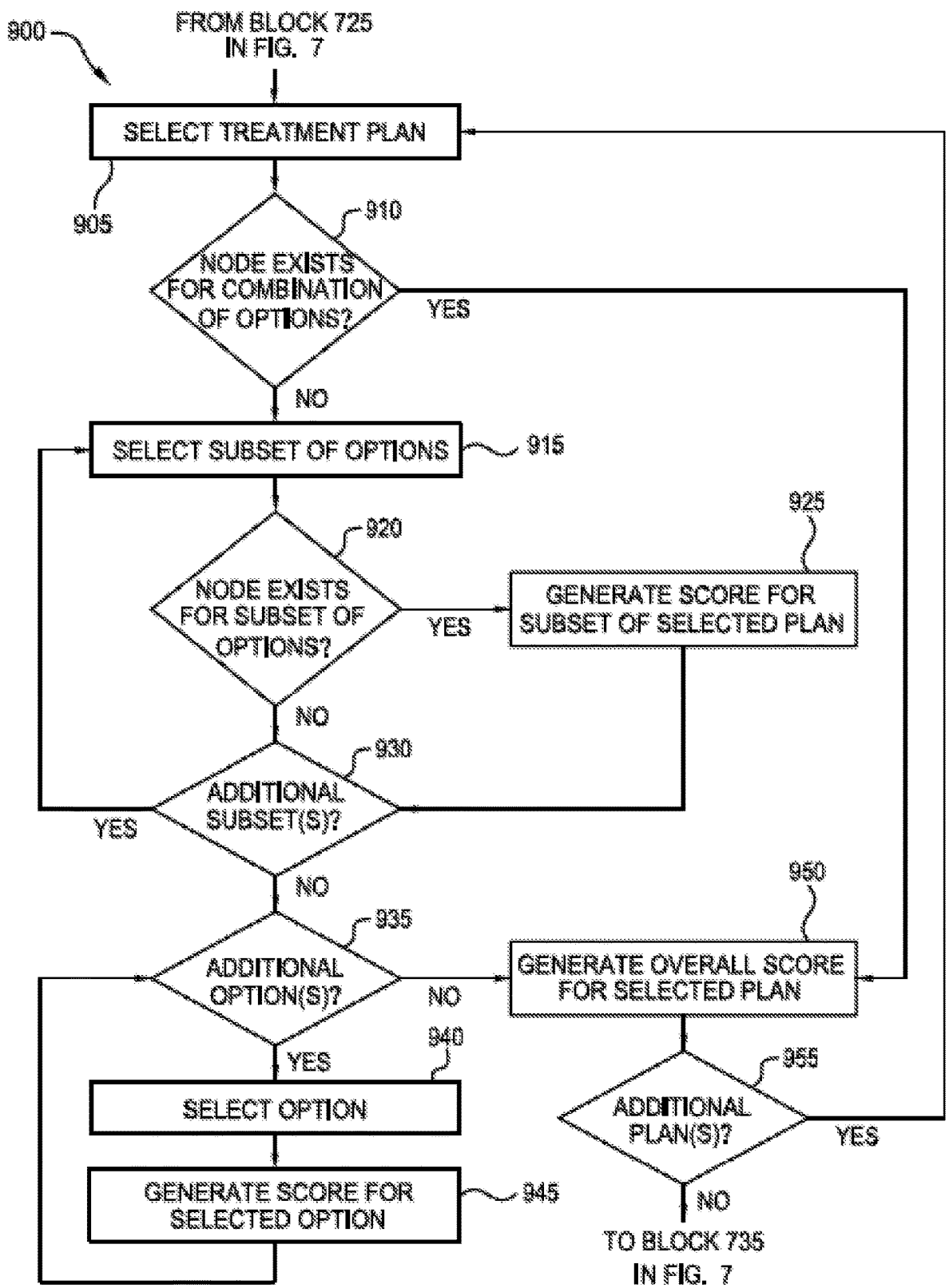
FIG. 9 is a flow diagram illustrating a method for evaluating treatment plans based on a knowledge graph, according to one embodiment disclosed herein.

FIG. 9 is a flow diagram illustrating a method 900 for evaluating treatment plans based on a knowledge graph, according to one embodiment disclosed herein. In one embodiment, the method 900 corresponds to block 730 in FIG. 7, and provides additional detail for evaluating the treatment plans. The method 900 begins at block 905, where the Therapy Evaluator 165 selects one of the treatment plans that were generated using a modified template. In some embodiments, the Therapy Evaluator 165 also evaluates treatment plans generated using the non-modified template, as discussed above. The method 900 then proceeds to block 910, where the Therapy Evaluator 165 determines whether the knowledge graph includes a node corresponding to the combination of therapy options included in the selected plan. That is, in the illustrated embodiment, the Therapy Evaluator 165 determines whether the exact combination of options has already been evaluated in the published literature, with the results being ingested and incorporated into the knowledge graph.

If the combination has already been tested, the method 900 proceeds to block 950, where the Therapy Evaluator 165 generates an overall score for the selected plan, based on this identified node. In an embodiment, this includes determining the overall efficacy of the therapy based on the efficacy indicated by the node. In some embodiments, determining the overall efficacy includes determining the relative efficacy as compared to other treatment combinations, as indicated by the edges in the graph. The method 900 then continues to block 955, where the Therapy Evaluator 165 determines whether there is at least one additional plan to be evaluated. If so, the method 900 returns to block 905. Otherwise, the method 900 terminates.

Returning to block 910, if the Therapy Evaluator 165 determines that the combination of treatments has not been evaluated before (e.g., because there is no node in the graph corresponding to the combination), the method 900 proceeds to block 915, where the Therapy Evaluator 165 selects a subset of the options. That is, the Therapy Evaluator 165 selects fewer than all of the options (e.g., all but one, half of them, etc.). In one embodiment, this selection is done randomly, and is repeated for each potential subset of options. The method 900 then proceeds to block 920, where the Therapy Evaluator 165 determines whether a node exists in the knowledge graph for the selected subset of therapies.

That is, the Therapy Evaluator 165 determines whether the selected combination has been evaluated in the published literature, such that a node in the knowledge graph was created to represent it. If so, the method proceeds to block 925.

At block 925, the Therapy Evaluator 165 generates a score for the selected subset of treatments, based on the identified node. In an embodiment, this includes determining the absolute efficacy of the subset of treatments based on the efficacy indicated by the node. In some embodiments, scoring the subset includes determining the relative efficacy of the subset, as compared to other treatment combinations (e.g., as indicated by the edges in the graph). The method 900 then continues to block 930, where the Therapy Evaluator 165 determines whether there is at least one additional subset to be evaluated. In an embodiment, if there are any untested subsets remaining, the method 900 returns to block 915, even if all of the treatment options have been scored. For example, suppose the treatment plan includes therapies A, B, C, and D. Suppose further that a node has been found corresponding to therapies A and B, and a second node has been found for therapies C and D. In an embodiment, the Therapy Evaluator 165 continues to evaluate subsets of the treatments (e.g., to search for a node corresponding to therapies B and C together, A and D together, three of the therapies together, and the like). In an embodiment, these separate scores (e.g., for each subset) are then aggregated, as discussed below in more detail.

If at least one additional subset remains, the method 900 returns to block 915. Otherwise, the method 900 proceeds to block 935. At block 935, the Therapy Evaluator 165 determines whether there are any treatment options for which a score has not yet been determined. In one embodiment, if a therapy was scored as part of a combination (e.g., a subset), the Therapy Evaluator 165 counts it as having been scored. In contrast, if a therapy or treatment option that was not scored as part of any subset of two or more therapies, the Therapy Evaluator 165 determines that it needs to be evaluated. In other embodiments, the Therapy Evaluator 165 evaluates all of the therapy options separately (e.g., without being combined with any other therapies). If there is at least one option to be evaluated, the method 900 proceeds to block 940.

At block 940, the Therapy Evaluator 165 selects one of the unscored options, and at block 945, the Therapy Evaluator 165 generates a score for the selected option. In an embodiment, generating the score for the individual option mirrors the process discussed above with reference to scoring the subsets and scoring the entire combination. The method 900 then returns to block 935. If, at block 935, the Therapy Evaluator 165 determines that there are no additional options that need to be scored, the method 900 proceeds to block 950, where the Therapy Evaluator 165 generates an overall score for the selected plan. In an embodiment, to generate the overall score, the Therapy Evaluator 165 aggregates the scores generated for each subset for which a node was present, as well as for each individual option that was scored.

In some embodiments, when aggregating the scores to generate an overall score, the Therapy Evaluator 165 assigns a weight to each score based on a variety of factors. In one embodiment, the weight is based in part on the number of options that were included in the score. For example, a score for a subset that covers three treatments will be assigned a relatively higher weight than a subset that only included two therapies. Similarly, in an embodiment, scores for individual treatment options receive a lower weight than subsets including two or more treatment options. In an embodiment, the weight is reduced to reflect reduced confidence that the score accurately reflects the ultimate desired combination. Thus, nodes that correspond to fewer of the treatment options are given lower weight, as it is uncertain whether the therapies may interact to improve or reduce the effect.

In some embodiments, if the knowledge graph does not include an exact match for one or more combinations or individual therapies, the Therapy Evaluator 165 also searches for similar or related combinations and treatment options. For example, if there is no node for the selected medication, the Therapy Evaluator 165 can analyze and score other medications in the same class. Similarly, if there is a node for the combination of medication X and surgery Y, but the selected plan includes medication Z and surgery Y, the Therapy Evaluator 165 can nevertheless score the node that includes medication X. In one embodiment, if the Therapy Evaluator 165 must rely on a similar or related therapy to generate a score, the weight of this score is likewise reduced to reflect the reduced certainty. Once the overall score has been generated for the selected treatment plan, the method 900 proceeds to block 955, where the Therapy Evaluator 165 determines whether there is at least one plan remaining to be scored. If so, the method 900 returns to block 905. Otherwise, the method 900 terminates.

Figure 10:
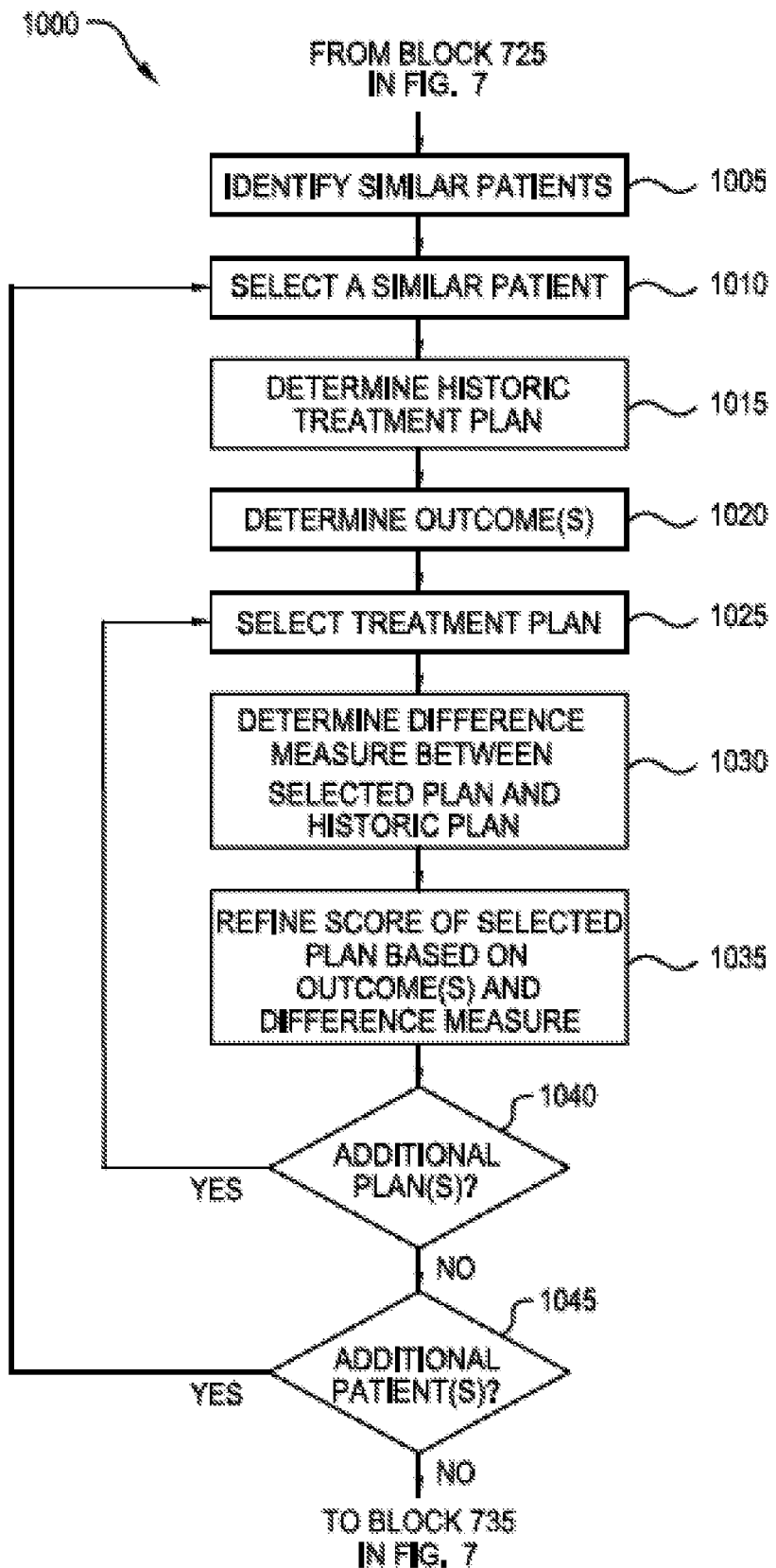
FIG. 10 is a flow diagram illustrating a method for evaluating treatment plans based on real world evidence, according to one embodiment disclosed herein.

FIG. 10 is a flow diagram illustrating a method 1000 for evaluating treatment plans based on real world evidence, according to one embodiment disclosed herein. In one embodiment, the method 900 corresponds to block 730 in FIG. 7, and provides additional detail for evaluating the treatment plans. The method 1000 begins at block 1005, where the Therapy Evaluator 165 evaluates a store of EMRs to identify patients that are similar to the index patient to be treated. In one embodiment, this involves identifying the cohort of the index patient. In some embodiments, the Therapy Evaluator 165 compares attributes of the index patient (which may be found in a patient profile, entered by the healthcare provider and/or patient, or identified in one or more EMRs associated with the index patient) with attributes included in the store of EMRs to identify clinically similar patients (e.g., patients that share one or more attributes with the index patient, who are also affected by or were previously affected by the same disorder or condition).

The method 1000 then proceeds to block 1010, where the Therapy Evaluator 165 selects one of the identified similar patients. At block 1015, the Therapy Evaluator 165 determines the treatment plan that was used to treat the selected patient. In an embodiment, the Therapy Evaluator 165 evaluates the EMRs associated with the selected patient (e.g., using one or more NLP techniques) to identify the associated historic treatment plan. In the illustrated embodiment, the plan used to treat the selected similar patient is referred to as a historic treatment plan. Note, however, that this does not imply that the treatment plan is outdated or no longer used. In an embodiment, the historic treatment plan may be identical to current plans being considered. Rather, the treatment plan used to treat the selected similar patient is labeled "historic" simply to distinguish it from the treatment plans currently being analyzed for the index patient. The method 1000 then proceeds to block 1020.

At block 1020, the Therapy Evaluator 165 determines the outcome(s) experienced by the selected patient, if available. For example, in one embodiment, the Therapy Evaluator 165 analyzes the associated EMRs using one or more NLP techniques to identify the outcomes. In one embodiment, if no outcomes are found (e.g., because the patient is still undergoing treatment and their condition has not yet changed), the patient records are discarded and not considered. In some embodiments, however, these records are utilized by the Therapy Evaluator 165 to generate scores for the plans currently being considered. For example, in an embodiment, the Therapy Evaluator 165 may modify the score based on how much time has elapsed for the selected patient since treatment began (which may indicate a minimum period of time before results can be expected).

The method 1000 then continues to block 1025, where the Therapy Evaluator 165 selects a treatment plan from the set of treatments that are currently being evaluated for the index patient. At block 1030, the Therapy Evaluator 165 determines a measure of difference or similarity between the selected current plan and the identified historic plan. In one embodiment, this includes determining additional components found in the historic plan that are not included in the selected plan, identifying treatments included in the current plan but not in the historic plan, and identifying components that are changed (e.g., substituting one therapy for a related or similar therapy). The method 1000 then proceeds to block 1035.

At block 1035, the Therapy Evaluator 165 generates or refines the score of the selected treatment plan based on the historic outcomes, as well as the difference measure. In an embodiment, the outcome(s) are weighted based on the difference measure, such that more similar historic plans are associated with a higher weight than less similar plans. In this way, the selected treatment plan is evaluated to determine potential outcomes based on RWE, where the evidence is weighted based on how similar or different the underlying treatment plan is to the current plan. In some embodiments, the outcomes are further weighted based on a similarity between the index patient and the selected similar patient (e.g., based on their respective attributes). In such an embodiment, less similar patients will be assigned lower weight than more similar patients.

The method 1000 then proceeds to block 1040, where the Therapy Evaluator 165 determines whether there is at least one additional proposed treatment plan to be analyzed. If so, the method 1000 returns to block 1025. Otherwise, the method 1000 continues to block 1045, where the Therapy Evaluator 165 determines whether there is at least one additional similar patient to be evaluated. If so, the method 1000 returns to block 1010. If not, the method 100 terminates. In this way, each potential plan is evaluated based on RWE, to determine a potential efficacy for the index patient. That is, in an embodiment, a RWE score is generated for a proposed treatment plan by aggregating outcome data for a number of similar patients.

In some embodiments, each treatment plan is evaluated using both the knowledge graph and using real world evidence. In some embodiments, the user (e.g., a healthcare provider) can select which methodology to utilize, or can review each separately. That is, in an embodiment, the user can review a score generated based on the knowledge graph, as well as a score based on RWE, in order to determine how each body of evidence affects the potential efficacy. In some embodiments, the Therapy Evaluator 165 aggregates the scores generated according to each method. For example, in one embodiment, the Therapy Evaluator 165 sums the scores, or averages them. In some embodiments, the knowledge graph and RWE are associated with respective weights, which affect the final aggregate score. In one embodiment, the user can specify these weights, to place additional importance on the type of evidence they prefer. In some embodiments, if the knowledge graph and/or the available RWE do not include evidence for a given treatment plan (e.g., the plan cannot be scored using the knowledge graph and/or RWE), the plan is discarded. In some embodiments, whether the plan is discarded is based in part on whether the user prefers evidence from the knowledge graph or RWE. For example, in one embodiment, if the user prefers RWE, the plan may be discarded if the RWE cannot yield a score, regardless of the evidence provided by the knowledge graph.

Figure 11:
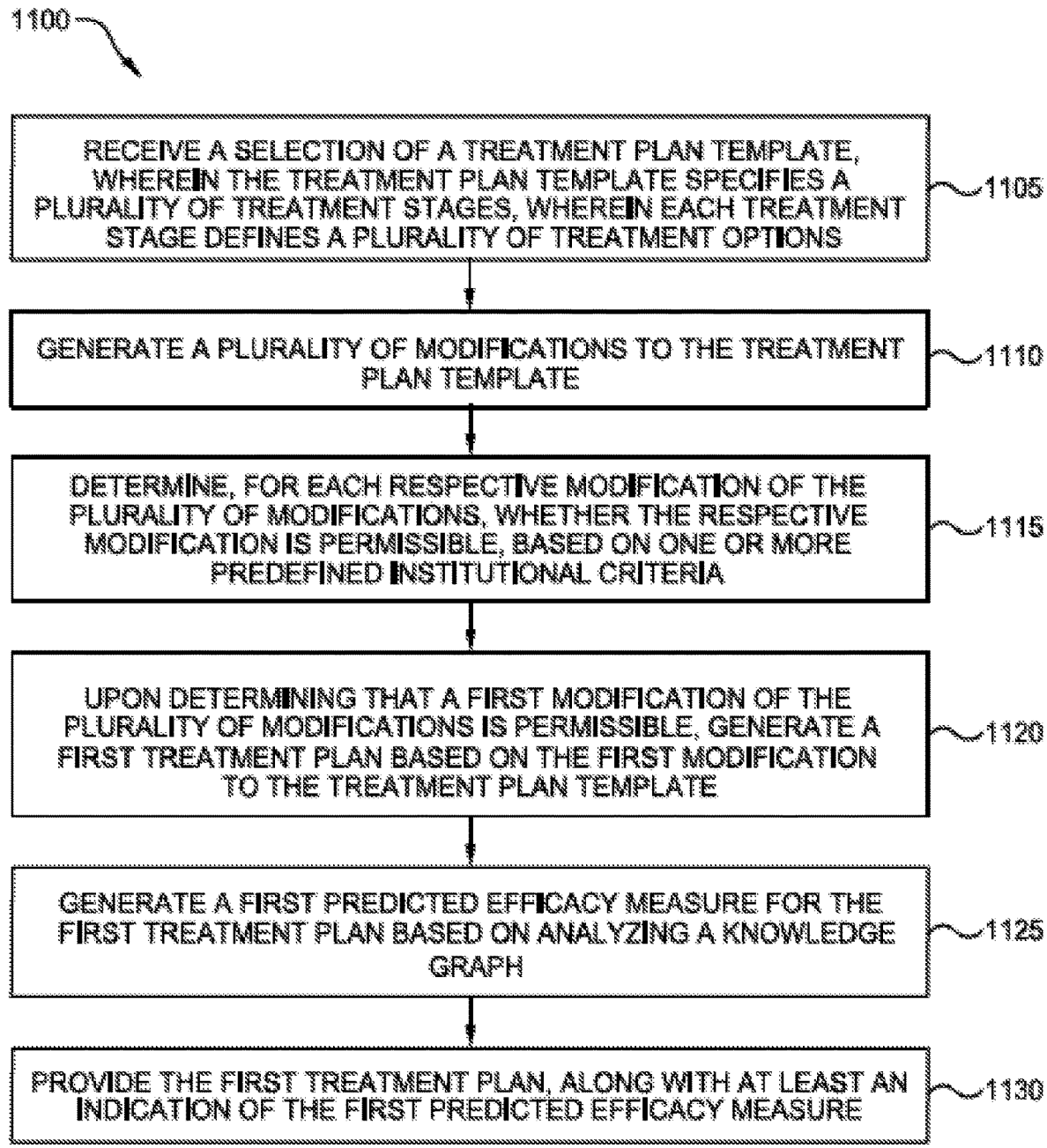
FIG. 11 is a flow diagram illustrating a method for modifying a plan template and evaluating the efficacy of the modified plans, according to one embodiment disclosed herein.

FIG. 11 is a flow diagram illustrating a method 1100 for modifying a plan template and evaluating the efficacy of the modified plans, according to one embodiment disclosed herein. The method 1100 begins at block 1105, where the Therapy Evaluator 165 receives a selection of a treatment plan template, wherein the treatment plan template specifies a plurality of treatment stages, wherein each treatment stage defines a plurality of treatment options. At block 1110, the Therapy Evaluator 165 generates a plurality of modifications to the treatment plan template. The method 1100 then proceeds to block 1115, where the Therapy Evaluator 165 determine, for each respective modification of the plurality of modifications, whether the respective modification is permissible, based on one or more predefined institutional criteria. At block 1120, upon determining that a first modification of the plurality of modifications is permissible, the Therapy Evaluator 165 generates a first treatment plan based on the first modification to the treatment plan template. The method 1100 then continues to block 1125, where the Therapy Evaluator 165 generates a first predicted efficacy measure for the first treatment plan based on evaluating a knowledge graph. Finally, at block 1130, the Therapy Evaluator 165 provides the first treatment plan, along with at least an indication of the first predicted efficacy measure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., a Therapy Evaluator 165) or related data available in the cloud. For example, the Therapy Evaluator 165 could execute on a computing system in the cloud and evaluate treatment template modifications. In such a case, the Therapy Evaluator 165 could analyze knowledge graphs and RWE to score treatment plans, and store treatment plan templates at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   receiving a selection of a treatment plan template, wherein the treatment plan template specifies a plurality of treatment stages, wherein each treatment stage defines a plurality of treatment options;
   generating a plurality of modifications to the treatment plan template;
   determining, for each respective modification of the plurality of modifications, whether the respective modification is permissible, based on one or more predefined institutional criteria;
   upon determining that a first modification of the plurality of modifications is permissible, generating a first treatment plan based on the first modification to the treatment plan template;
   generating a first predicted efficacy measure for the first treatment plan by operation of one or more processors, based on analyzing a knowledge graph; and
   providing the first treatment plan, along with at least an indication of the first predicted efficacy measure.

2. The method of claim 1, wherein the first modification comprises adding a new treatment stage to the plurality of treatment stages.

3. The method of claim 1, wherein the first modification comprises changing a first treatment stage of the plurality of treatment stages, wherein changing the first treatment stage comprises adding a new option to the plurality of treatment options defined by the first treatment stage.

4. The method of claim 1, wherein the first modification comprises removing a first treatment stage from the plurality of treatment stages.

5. The method of claim 1, the method further comprising determining that a second modification of the plurality of modifications is impermissible based on determining that one or more of the predefined institutional criteria require a first treatment stage to be present, wherein the second modification includes removing the first treatment stage from the plurality of treatment stages.

6. The method of claim 1, the method further comprising:
   determining that the first predicted efficacy measure is below a predefined threshold; and
   requesting manual approval of the first treatment plan.

7. The method of claim 1, wherein generating the first predicted efficacy measure further comprises:
   identifying one or more clinically similar patients to a first patient for whom the first treatment plan is being designed; and
   determining, for each of the one or more clinically similar patients, a respective treatment plan and a respective outcome.

8. The method of claim 1, the method further comprising:
   receiving a new treatment plan, wherein the new treatment plan comprises a plurality of treatment stages, wherein the plurality of treatment stages are not included in an existing treatment plan;
   determining whether the new treatment plan is permissible, based on the predefined institutional criteria; and
   generating a second predicted efficacy measure for the new treatment plan based on analyzing the knowledge graph.

9. A computer-readable storage medium having computer-readable program code embodied therewith, the computer-readable program code executable by one or more computer processors to perform an operation comprising:
   receiving a selection of a treatment plan template, wherein the treatment plan template specifies a plurality of treatment stages, wherein each treatment stage defines a plurality of treatment options;
   generating a plurality of modifications to the treatment plan template;
   determining, for each respective modification of the plurality of modifications, whether the respective modification is permissible, based on one or more predefined institutional criteria;
   upon determining that a first modification of the plurality of modifications is permissible, generating a first treatment plan based on the first modification to the treatment plan template;
   generating a first predicted efficacy measure for the first treatment plan based on analyzing a knowledge graph; and
   providing the first treatment plan, along with at least an indication of the first predicted efficacy measure.

10. The computer-readable storage medium of claim 9, wherein the first modification comprises changing a first treatment stage of the plurality of treatment stages, wherein changing the first treatment stage comprises adding a new option to the plurality of treatment options defined by the first treatment stage.

11. The computer-readable storage medium of claim 9, the operation further comprising determining that a second modification of the plurality of modifications is impermissible based on determining that one or more of the predefined institutional criteria require a first treatment stage to be present, wherein the second modification includes removing the first treatment stage from the plurality of treatment stages.

12. The computer-readable storage medium of claim 9, the operation further comprising:

determining that the first predicted efficacy measure is below a predefined threshold; and requesting manual approval of the first treatment plan.

13. The computer-readable storage medium of claim 9, wherein generating the first predicted efficacy measure further comprises:

identifying one or more clinically similar patients to a first patient for whom the first treatment plan is being designed; and determining, for each of the one or more clinically similar patients, a respective treatment plan and a respective outcome.

14. The computer-readable storage medium of claim 9, the operation further comprising:

receiving a new treatment plan, wherein the new treatment plan comprises a plurality of treatment stages, wherein the plurality of treatment stages are not included in an existing treatment plan;

determining whether the new treatment plan is permissible, based on the predefined institutional criteria; and generating a second predicted efficacy measure for the new treatment plan based on analyzing the knowledge graph.

15. A system comprising:

one or more computer processors; and a memory containing a program which when executed by the one or more computer processors performs an operation comprising:

receiving a selection of a treatment plan template, wherein the treatment plan template specifies a plurality of treatment stages, wherein each treatment stage defines a plurality of treatment options;

generating a plurality of modifications to the treatment plan template;

determining, for each respective modification of the plurality of modifications, whether the respective modification is permissible, based on one or more predefined institutional criteria;

upon determining that a first modification of the plurality of modifications is permissible, generating a first treatment plan based on the first modification to the treatment plan template;

generating a first predicted efficacy measure for the first treatment plan based on analyzing a knowledge graph; and providing the first treatment plan, along with at least an indication of the first predicted efficacy measure.

16. The system of claim 15, wherein the first modification comprises changing a first treatment stage of the plurality of treatment stages, wherein changing the first treatment stage comprises adding a new option to the plurality of treatment options defined by the first treatment stage.

17. The system of claim 15, the operation further comprising determining that a second modification of the plurality of modifications is impermissible based on determining that one or more of the predefined institutional criteria require a first treatment stage to be present, wherein the second modification includes removing the first treatment stage from the plurality of treatment stages.

18. The system of claim 15, the operation further comprising:

determining that the first predicted efficacy measure is below a predefined threshold; and requesting manual approval of the first treatment plan.

19. The system of claim 15, wherein generating the first predicted efficacy measure further comprises:

identifying one or more clinically similar patients to a first patient for whom the first treatment plan is being designed; and determining, for each of the one or more clinically similar patients, a respective treatment plan and a respective outcome.

20. The system of claim 15, the operation further comprising:

receiving a new treatment plan, wherein the new treatment plan comprises a plurality of treatment stages, wherein the plurality of treatment stages are not included in an existing treatment plan;

determining whether the new treatment plan is permissible, based on the predefined institutional criteria; and generating a second predicted efficacy measure for the new treatment plan based on analyzing the knowledge graph.

\* \* \* \* \*